US010042026B2

(12) United States Patent
Li et al.

(10) Patent No.: US 10,042,026 B2
(45) Date of Patent: Aug. 7, 2018

(54) APPARATUS AND METHODS OF DATA INVERSION

(75) Inventors: Jing Li, Houston, TX (US); Songhua Chen, Katy, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 668 days.

(21) Appl. No.: 14/414,031

(22) PCT Filed: Jul. 24, 2012

(86) PCT No.: PCT/US2012/048009
§ 371 (c)(1),
(2), (4) Date: Jan. 9, 2015

(87) PCT Pub. No.: WO2014/018022
PCT Pub. Date: Jan. 30, 2014

(65) Prior Publication Data
US 2015/0177352 A1    Jun. 25, 2015

(51) Int. Cl.
*G01V 3/00* (2006.01)
*G01R 33/54* (2006.01)
*G01N 24/08* (2006.01)
*G06F 17/11* (2006.01)

(52) U.S. Cl.
CPC ........... *G01R 33/54* (2013.01); *G01N 24/081* (2013.01); *G06F 17/11* (2013.01)

(58) Field of Classification Search
CPC .............. G01R 33/543; G01R 33/5659; G01R 33/3415; G01R 33/36; A61B 5/055
USPC ........................................................ 324/309
See application file for complete search history.

(56) References Cited

U.S. PATENT DOCUMENTS

| 5,517,115 | A  | 5/1996  | Prammer       |
|-----------|----|---------|---------------|
| 6,084,408 | A  | 7/2000  | Chen et al.   |
| 6,147,489 | A  | 11/2000 | Freedman et al.|
| 6,229,308 | B1 | 5/2001  | Freedman      |
| 6,523,117 | B2 | 2/2003  | Oki et al.    |

OTHER PUBLICATIONS

"Australian Application Serial No. 2012385986, Response filed Jun. 22, 2016 to Examination Report No. 1 dated Jan. 21, 2016", 25 pgs.
"Australian Application Serial No. 2012385986, Subsequent Examiners Report dated Jul. 5, 2016", 3 pgs.
"Mexican Application Serial No. MX/a/2015/001069, Office Action dated Mar. 17, 2016", (w/ English Summary), 4 pgs.
"Mexican Application Serial No. MX/a/2015/001069, Response filed Aug. 3, 2016 to Office Action dated Mar. 17, 2016", (w/ English Translation of Amended Claims), 21 pgs.
Dunn, K.-J., et al., "Chapter 6—NMR data acquisition and inversion", *Handbook of Geophysical Exploration: Seismic Exploration*, vol. 32, (2002), 165-196.
"Australian Application Serial No. 2012385986; Third Examination Report dated Oct. 17, 2016.", 3 pages.

(Continued)

*Primary Examiner* — Walter L Lindsay, Jr.
*Assistant Examiner* — Frederick Wenderoth
(74) *Attorney, Agent, or Firm* — Gilliam IP PLLC

(57) ABSTRACT

Various embodiments include apparatus and methods to determine properties of a structure using data measurements on the structure. These measurements can be subjected to an inversion process that uses an optimization procedure conducted in a continuous function space. Additional apparatus, systems, and methods are disclosed.

25 Claims, 9 Drawing Sheets

(56) References Cited

OTHER PUBLICATIONS

"Gulf Cooperation Council Application Serial No. 2013-24904, First Examination Report dated Mar. 23, 2017.", 5 pages.
"International Application Serial No. PCT/US2012/048009, International Search Report dated Jul. 8, 2013", 6 pgs.
"International Application Serial No. PCT/US2012/048009, Invitation to Pay Additional Fees and Partial Search Report dated May 24, 2013", 6 pgs.
"International Application Serial No. PCT/US2012/048009, Written Opinion dated Jul. 8, 2013", 19 pgs.
Beleg, Murat, et al., "Efficient determination of multiple regularization parameters in a generalized L-curve framework", Inverse Problems, 18(4), (2002), 1161-1183.
Bertero, M., et al., "Linear inverse problems with discrete data. I. General formulation and singular system analysis", Inverse Problems, 1(4), (1985), 301-330.
Calvetti, D., et al., "L-Curve and Curvature Bounds for Tikhonov Regularization", Numerical Algorithms, 35(2-4), (2004), 301-314.
Chen, Songhua, et al., "Improvement of NMR Multi-Dimensional Inversion Methods for Accurate Petrophysical and Fluid Quantification Analyses", Transactions of the SPWLA Fiftieth Annual Logging Symposium, (2009), 1-12.
Dunn, K J, et al., "Nuclear Magnetic Resonance Petrophysical and Logging Applications", In: Handbook of Geophysical Exploration: vol. 32—Seismic Exploration, Elsevier Science Ltd., (2002), 156-182.
Galvosas, Petrik, et al., "On the use of 2D correlation and exchange NMR spectroscopy in organic porous materials", Magnetic Resonance Imaging, 25(4), (May 2007), 497-500.
Hansen, Per Christian, "Lecture 3: Regularization Parameters", Suggestion for a Short Course in Discrete Inverse Problems, [online]. Retrieved from the Internet: <URL:http://www2.imm.dtu.dk/˜pcha/DIP/chap5.pdf>, (2010), 17 pgs.
Veevaete, Maarten, et al., "Applications of Earth's Field NMR to Porous Systems and Polymer Gels", Dissertation zur Erlangung des Grades eines Doktors der Naturwissenschaften, [online]. Retrieved from the Internet: <URL:http://d-nb.info/992938694/34>, (2008), 144 pgs.
Washburn, K E, et al., "Pore characterization through propagator-resolved transverse relaxation exchange", Physical Review E, 77(5), (2008), 051203-1-051203-13.
"Australian Application Serial No. 2012385986, Examination Report dated Jan. 21, 2016", 3 pgs.
"European Application Serial No. 12741234.4, Office Action dated Mar. 5, 2015", 2 pgs.
"European Application Serial No. 12741234.4, Response filed Jul. 31, 2015 to Office Action dated Mar. 5, 2015", 20 pgs.
"International Application Serial No. PCT/US2012/048009, International Preliminary Report on Patentability dated Feb. 5, 2015", 21 pgs.

APPARATUS AND METHODS OF DATA INVERSION

PRIORITY APPLICATIONS

This application is a U.S. National Stage Filing under 35 U.S.C. 371 from International Application No. PCT/US2012/048009, filed on 24 Jul. 2012, and published as WO 2014/018022 A1 on 30 Jan. 2014; which application and publication are incorporated herein by reference in their entirety.

TECHNICAL FIELD

The present invention relates generally to apparatus for making and evaluating measurements.

BACKGROUND

In measurements on systems, an exponential function may arise whenever a quantity grows or decays at a rate proportional to its current value. Properties of many natural phenomena can be described by exponential functions. For a system that is a mixture of such decay rates, a function for the system can be expressed as multi-exponential decay function:

$$E = \sum_{l=1}^{I} A_l \exp(-t/T_l) \quad (1)$$

An inverse Laplace transform applied to the measured data having the multi-exponential behavior can be used to provide the distribution of A. Such application is not limited to one-dimensional (1D) analysis, but can be applied to two-dimensional (2D) and three-dimensional (3D) analysis. Problems that can be solved with the inverse Laplace transform method include inversion of echo trains to obtain 1D relaxation time and a 2D diffusion-relaxation distribution. There are other types of problems that can be formed in a similar single or multiple dimensional inverse Laplace transform problem. The inverse Laplace transform is applicable to other problems in which measurement data can be expressed by a multi-exponential function.

Deriving petrophysical information from nuclear magnetic resonance (NMR) logs often starts with an echo train inversion using a multi-exponential model. An NMR inversion technique involves fitting parameters and variables to the measured echo trains through an optimization procedure in the discrete space. The optimization procedure includes a series of time-consuming matrix multiplications for each measurement data sequence (echo trains), which can cause intolerable processing inefficiency in processing NMR multi-dimensional parameter space inversions.

An echo train in NMR measurement can be expressed by, $$M(t, Tw, G) = \sum_{i=1}^{I}\sum_{j=1}^{J} m_{ij}\left(1 - e^{-\frac{Tw}{RT_{2i}}}\right)e^{-\left[\frac{1}{T_{2i}} + \frac{(D_j \cdot G \cdot \gamma \cdot TE)^2}{12}\right]t}, \quad (2)$$

where M is the echo amplitude, $m_{ij}$ the unknown partial porosities on a grid with index (i, j), $D_j$ the fluid diffusivity, $T_w$ the wait time, $\gamma$ the gyromagnetic ratio, G the magnetic field gradient, TE the time spacing between echoes in an echo train, and R=T1/T2. T1 and T2 are the longitudinal and transversal relaxation times, respectively. Determination of the unknown partial porosity $m_{ij}$ according to the measured echo train amplitude is an inversion problem. Through the process of inversion, the spin-echo decay data can be converted to a T2 distribution. This distribution represents a "most likely" distribution of T2 values that produce the echo train. With proper calibration and account for hydrogen index of the fluids in the pore space, the area under a T2 distribution curve is equal to the porosity. This distribution can be correlated with a pore size distribution when the rock is 100% water saturated. However, if hydrocarbons are present, the T2 distribution will be altered depending on the hydrocarbon type, viscosity, and saturation.

The inversion problem to determine the unknown partial porosity $m_{ij}$ can be mathematically described by, $$\min\left\{\sum_{p=1}^{P}\left(w_p \sum_{q=1}^{Q_p}\left(\sum_{i=1}^{I}\sum_{j=1}^{J} m_{ij}\left(1 - e^{-\frac{Tw_p}{RT_{2i}}}\right)e^{-\left[\frac{1}{T_{2i}} + \frac{(D_j \cdot G_p \cdot \gamma \cdot TE)^2}{12}\right]t_{q_p}} - g_{q_p}\right)^2\right) + \|W(\alpha) \cdot \overline{m}\|^2\right\}, \quad (3)$$

where p is the echo train index and P is the total number of different echo trains in a data acquisition sequence; $w_p$ is the weight applied the $p^{th}$ echo train. This minimization problem is usually solved by the least squares method, where $\overline{m}$ is the vector containing all the unknowns $m_{ij}$, i=1, 2, . . . I, j=1, 2, . . . J, and W($\alpha$) is a regularization matrix. One of the key procedures of the least squares method is to convert the expression (3) into the matrix equation (4)

$$\sum_{p=1}^{P}\{[(A_{L \times JI})_p^T \cdot (A_{L \times JI})_p + W^T W]\overline{m} - (A_{L \times JI})_p^T \cdot \overline{g}_p\} = 0, \quad (4)$$

where L is the total number of echoes in the echo train; JI=J·I denotes the number of the unknowns to be inverted, and the vector $\overline{g}_p$ contains the measured amplitude of the $p^{th}$ echo train. Due to the overwhelming large number of the matrix elements, the matrix operations performed in equation (4) is time-consuming, significantly slowing down the signal processing speed. Furthermore, processing using a huge amount of numerical operations, as is typical in such an analysis, can accumulate serious quantitative errors.

The second term in equation (3) is a regularization term. W($\alpha$) means that the entries of matrix W are functions of the regularization factor $\alpha$ (alpha). A simple example of W($\alpha$) is an identity matrix multiplied by $\alpha$. The inclusion of a regularization term is important to many inversion problems using the least squares method, because least squares solutions are affected by data and rounding errors. The regularization dampens the error effects. It can be important to use adequate regularization such that it de-sensitizes noise influence while not introducing significant misfit. In general, an adjustable regularization coefficient is used. Normally, this adjustable parameter, $\alpha$, is often determined by a cumbersome process involving multiple fitting trials with varying $\alpha$.

Mathematical relation (3) can be expressed as, $$(A + W(\alpha)^T W(\alpha))x = B \quad (5)$$

where $x = [m_{11}, m_{12}, \ldots, m_{1J}, \ldots, m_{I1}, m_{I2}, \ldots, m_{IJ}]^T$. With the insertion of the regularization term, the solution vector x from equation (5) becomes a function of the factor α, denoted as x(α). Similarly, the error vector Ax–B also becomes a function of α, denoted as Ax(α)–B. If the norm of the error vector ||Ax(α)–B|| and the norm of the solution vector ||x(α)|| are used as the horizontal and vertical axis respectively to plot a curve, it will present an L-shape as shown in FIG. 1. The point on the curve with the maximum curvature corresponds to the optimal α. On the other hand, if a function of α is defined as $$d(\alpha)=\sqrt{||Ax(\alpha)-B||^2+||x(\alpha)||^2}, \quad (6)$$

then the plot of d(α) with respect to α can produce a parabolic-shaped curve, as shown in FIG. 2. The α value that minimizes d(α) corresponds to the stability of the inversion equation and the solution error. This α value is also referred to as the optimal α. Both the use of the L-curve and the use of the parabolic shaped curve can predict an optimal α based on the above criterion of the respective curves. Both methods may predict similar results. FIG. 3 shows an example where the maximum curvature of the L-curve (curve 342) and the minimum value of d(α) (curve 341) occur at almost the same α point. So as long as the correlation of ||Ax(α)–B|| with α and the correlation of ||x(α)|| with α are calculated using a list of trial α values, an optimal α can be determined either through the maximum curvature of the L-Curve or the minimum point of the parabolic type curve. Which of the above two methods, L-curve or parabolic shaped curve, is employed may depend on the performance of application in a given project. However, to obtain each point for the L-curve and for the parabolic curves requires performance of one iteration of the inversion process per point. As a result, calculation of multiple points in a curve takes a significant amount of time.

DETAILED DESCRIPTION

The following detailed description refers to the accompanying drawings that show, by way of illustration and not limitation, various embodiments in which the invention may be practiced. These embodiments are described in sufficient detail to enable those skilled in the art to practice these and other embodiments. Other embodiments may be utilized, and structural, logical, and electrical changes may be made to these embodiments. The various embodiments are not necessarily mutually exclusive, as some embodiments can be combined with one or more other embodiments to form new embodiments. The following detailed description is, therefore, not to be taken in a limiting sense.

In multi-exponential behavior of measured data, analysis can be conducted using an inversion technique that involves fitting parameters and variables to the measured data through an optimization procedure in discrete space. The optimization procedure can include a series of time-consuming matrix multiplications for each measurement data sequence, which can cause processing inefficiency in processing multi-dimensional parameter space inversions. The optimization procedure can include use of the least squares method.

In various embodiments, a continuous-function-space (CFS) optimization process can be implemented to conduct data inversion. Optimization matrix elements can be derived analytically in the continuous function space. This analytic approach can provide for the avoidance of tedious matrix operations and can greatly reduce the matrix processing time without incurring negative consequences. An additional process can be used to provide a fast method for predicting an optimal regularization factor that can be used to conduct the optimization for the data inversion. This analytic approach can be implemented using a known function derived by interpolation to the measured data, where the known function can be used in a matrix equation generated in the optimization problem. With the known function structured as an analytically integrable function, all matrix elements may be calculated analytically. Such integrable functions can include, but are not limited to, linear interpolation functions, S-Spline interpolation functions, or exponential interpolation functions.

Figure 1:
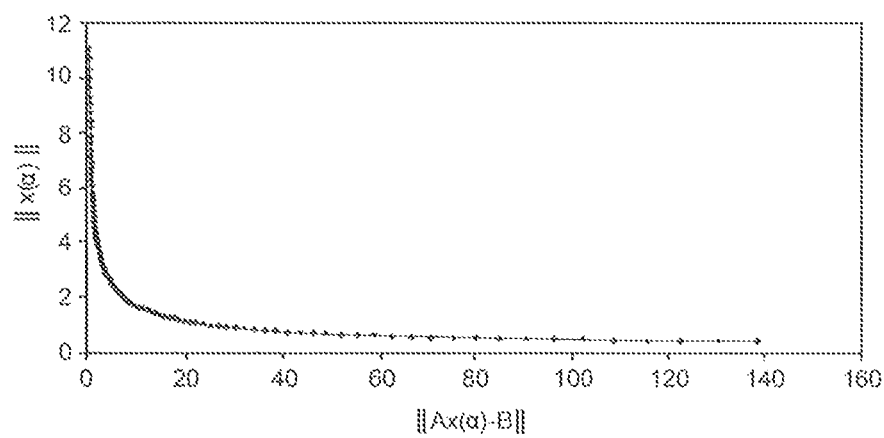
FIG. 1 shows a curve of a norm of a solution vector as a function of a regularization factor with respect to a norm of an error vector as a function of the regularization factor, in accordance with various embodiments.
Figure 2:
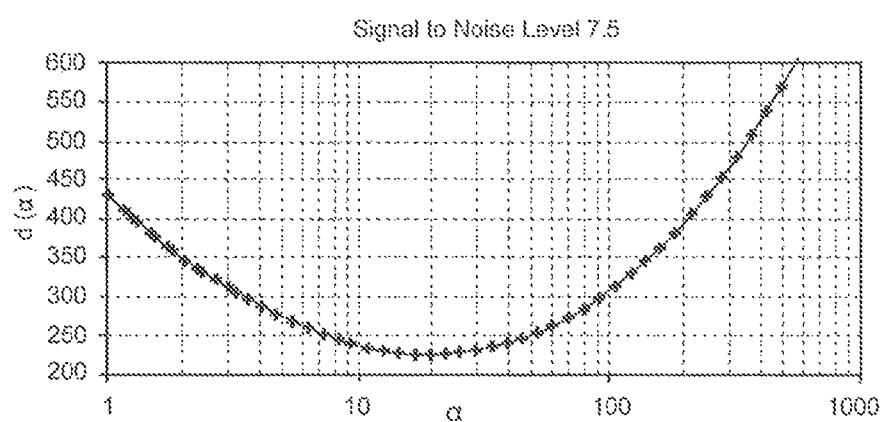
FIG. 2 shows a curve of a composite function of the error vector and the solution vector of FIG. 1 with respect to the regularization factor, in accordance with various embodiments.
Figure 3:
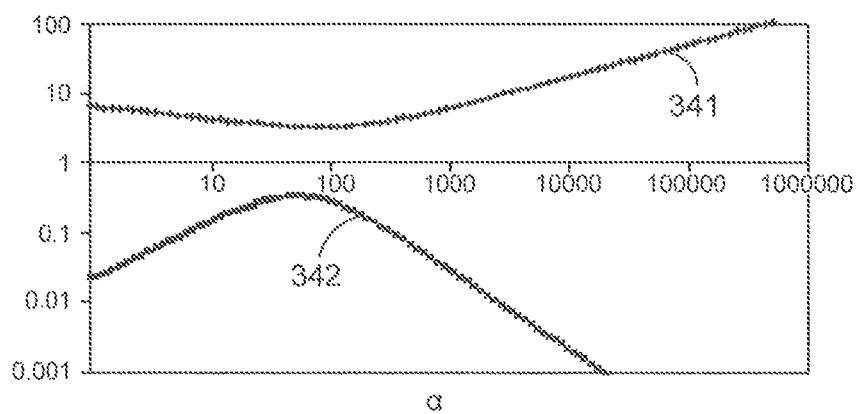
FIG. 3 shows example curves of the L-curve method and the parabolic curve with respect to the regularization factor, in accordance with various embodiments.
Figure 4:
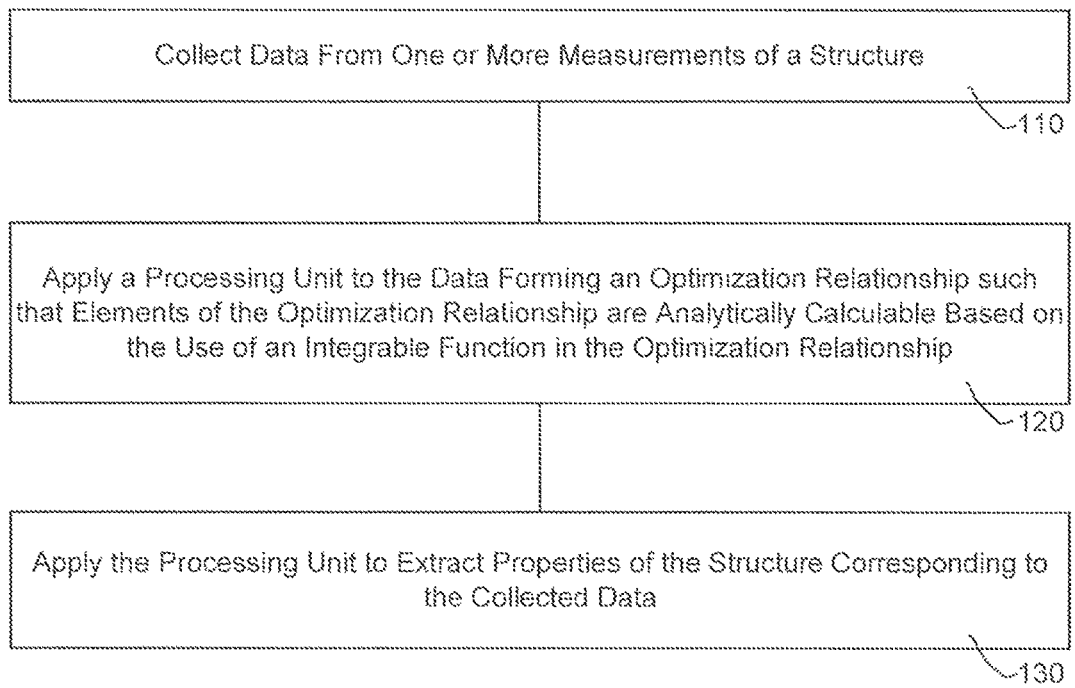
FIG. 4 shows features of an example method of inverting discrete measurement data in continuous-function-space, in accordance with various embodiments.

FIG. 4 shows features of an example embodiment of a method of inverting discrete measurement data in continuous-function-space. At 110, data from one or more measurements of a structure is collected. The data may exhibit multi-exponential decay. The decay curves may be equally spaced decay curves. At 120, a processing unit is applied to the data forming an optimization relationship based on the use of an integrable function in the optimization relationship. The use of an integrable function in the optimization relationship can be conducted such that elements of the optimization relationship are analytically calculable. The integrable function can be derived from the collected data. Deriving the integrable function can be conducted by generating an integrable interpolation function from the data. Generating the integrable interpolation function can include generating one or more of a linear interpolation function, an S-Spline interpolation function, or exponential interpolation function. At 130, the processing unit is applied to extract values of properties of the structure corresponding to the collected data.

In various embodiments, a method of analyzing nuclear magnetic resonance logging data with respect to a region of a borehole employs a continuous-function-space (CFS) optimization process to conduct NMR inversion. Optimization matrix elements can be derived analytically in the continuous function space. This analytic approach can provide for the avoidance of tedious matrix operations and can greatly reduce the matrix processing time without incurring negative consequences. An additional process can be used to provide a fast method for predicting an optimal regularization factor that can be used to conduct the optimization for the NMR inversion. This method is operable to speed up the NMR inversion significantly.

Figure 5:
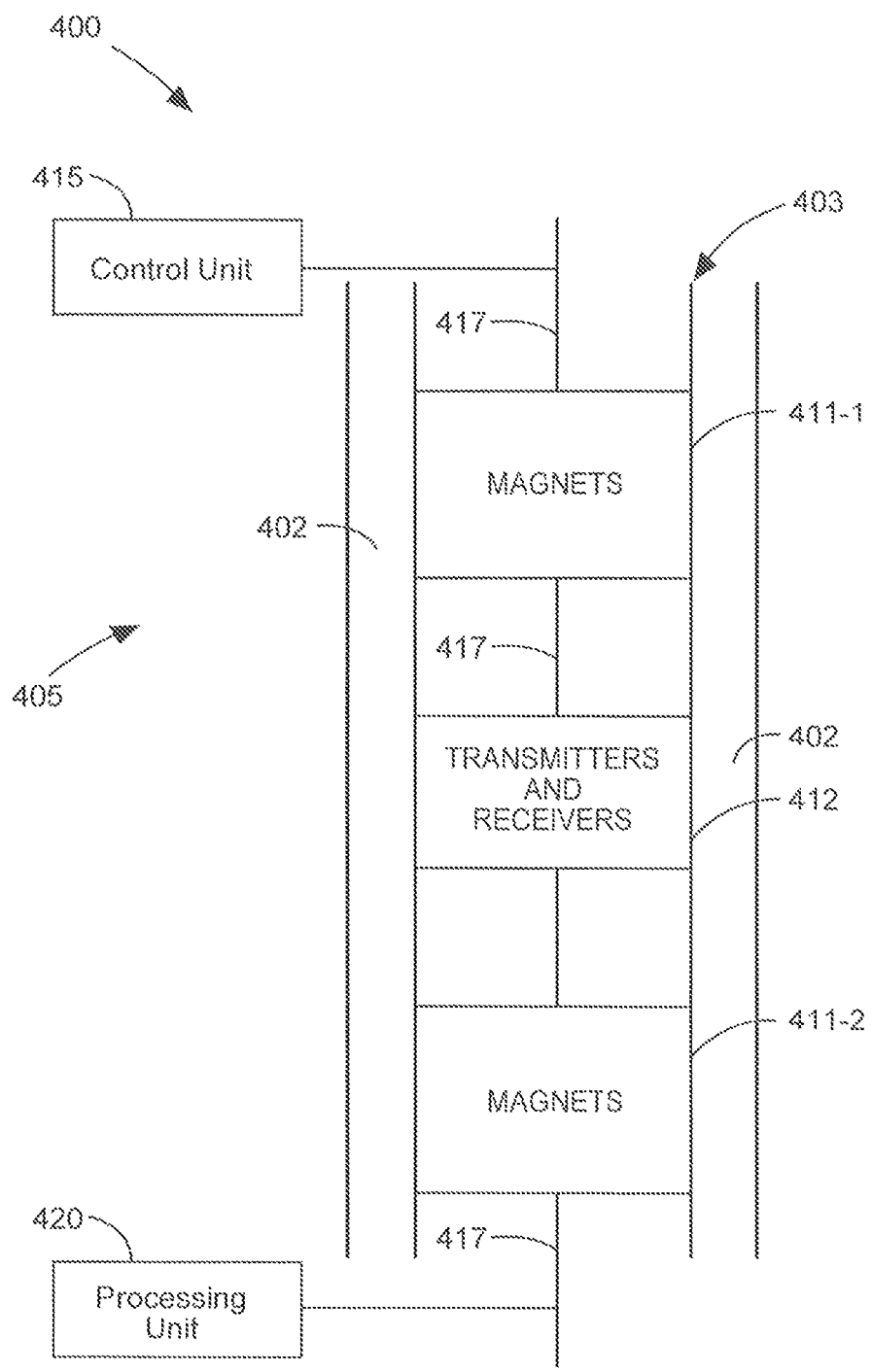
FIG. 5 shows a block diagram of an example system structured to determine properties of a region of a borehole subjected to nuclear magnetic resonance measurements, in accordance with various embodiments.

FIG. 5 shows a block diagram of an example embodiment of a system 400 structured to determine properties of a region of a borehole 402 subject to nuclear magnetic resonance measurements. The system 400 includes a nuclear magnetic resonance tool 405 having a tool structure 403, a control unit 415, and a processing unit 420. The tool structure 403 has an arrangement of magnets 411-1 and 411-2 and transmitters and receivers 412 under the control of control unit 415. The transmitters and receivers 412 can be realized as transceivers. These transmitters and receivers 412 may be arranged with respect to a longitudinal axis 417 of the tool structure 403, though they need not be arranged relative to the longitudinal axis 417. The control unit 415 can be operable to manage generation and collection of signals from the one or more transmitters and receivers 412. The processing unit 420 of the system 400 can be structured to process the received signals to determine properties of the region of the borehole 402 investigated by the nuclear magnetic resonance tool 405. The nuclear magnetic resonance tool 405 can be structured with the processing unit 420 and the control unit 415 integrated with the tool structure 403 or structured as distributed components. Distributed components can include components housed on the surface at a drilling location or downhole. In addition, the processing unit 420 and the control unit 415 can be realized as an integrated unit housed on the surface at a drilling location or downhole.

In various embodiments, the nuclear magnetic resonance tool 405 or other nuclear magnetic resonance tool can be used to perform a method comprising: collecting data from measured echo trains in a nuclear magnetic resonance measurement procedure conducted on a region of a borehole; applying a processing unit to the data forming an optimization relationship including unknown partial porosities of the region such that elements of the optimization relationship are analytically calculable based on the use of an integrable function in the optimization relationship, the integrable function derived from the collected data; and applying the processing unit to extract properties of the region corresponding to the collected data. The method can include deriving the integrable function by generating an integrable interpolation function from the data. Generating the integrable interpolation function can include generating one or more of a linear interpolation function, an S-Spline interpolation function, or exponential interpolation function. The optimization relationship can be formed as an optimization matrix relationship in a data storage device. The data storage device can include electronic or optical memories, a series of data registers, or other devices in which data can be moved in and out of for processing data collected by a nuclear magnetic resonance tool.

In various embodiments, the nuclear magnetic resonance tool 405 or other nuclear magnetic resonance tool can be used to perform a method comprising: collecting data from measured echo trains in a nuclear magnetic resonance measurement procedure conducted on a region of a borehole; and operating a processing unit such that the processing unit conducts operations including conducting operations to facilitate inversion of measured NMR data. The operations can include: operating on the data forming an optimization relationship including unknown partial porosities of the region and a regularization matrix such that a vector of the unknown partial porosities and an error vector are based on a regularization factor, the error vector generated from the optimization relationship; generating a first linear correlation between the logarithm corresponding to the vector of the unknown partial porosities and a logarithm corresponding to the regularization factor using a number of initially selected values of the regularization factor; generating a second linear correlation between a logarithm corresponding to the error vector and the logarithm corresponding to the regularization factor using the number of initially selected values of the regularization factor; generating a first vector of the unknown partial porosities based on the first linear correlation and generating a second error vector based on the second linear correlation generating points of a curve using the first vector and the second error vector and determining an approximately optimal value of the regularization factor using the points of the curve, the approximately optimal value applied to the optimization relationship to conduct an inversion of the data; and extracting properties of the region corresponding to the collected data from the inversion.

In various embodiments, a processing unit, such as but not limited to processing unit 420, can be structured to conduct optimizing procedures in a continuous function space to avoid huge matrix operations. To accomplish such processing, mathematical relation (3) can be derived in the CFS as, $$\min\left\{\int\left(\sum_{i=1}^{I}\sum_{j=1}^{J}m_{ij}\left(1-e^{-\frac{T_w}{RT_{2i}}}\right)e^{-\left[\frac{1}{T_{2i}}+\frac{(D_j\cdot G\cdot\gamma\cdot TE)^2}{12}\right]t}-g(t)\right)^2 dt + \|W\cdot\overline{m}\|^2\right\}, \quad (7)$$

where g(t) can be generated from the measured echo trains providing a known function. The known function can be derived by interpolation to the measured echo trains. The optimization problem described by expression (7) can be converted into the matrix equation by the least square method in the continuous function space as, $$\left(\sum_{p=1}^{P} C^{(p)} + W^T W\right)\overline{m} = \sum_{p=1}^{P} B^{(p)} \quad (8)$$

where $C^{(p)}$ and $B^{(p)}$ are the matrix and signal vector of the $p^{th}$ echo train, respectively. Because the integrand in equation (7) is analytically integrable, when converting it into the matrix equation (8), all elements in each matrix $C^{(p)}$ can be calculated analytically by equations (9-1) and (9-2) given by, $$c_{kn}^{(p)} = \left(1 - e^{-\frac{Tw(p)}{RT_{2u}}}\right)\int_{T_{start}^{(p)}}^{T_{end}^{(p)}} e^{-\frac{t}{T_{2u}}} \cdot e^{-\frac{t}{T_{2x}}} \cdot e^{-\left[(D_v+D_y)\frac{(\gamma G^{(p)}TE^{(p)})^2}{12}\right]t} dt, \quad (9\text{-}1)$$

$$= \left(1 - e^{-\frac{Tw(p)}{RT_{2u}}}\right)\frac{\left(e^{-\beta_{kn}^{(p)}\cdot T_{start}^{(p)}} - e^{-\beta_{kn}^{(p)}\cdot T_{end}^{(p)}}\right)}{\frac{1}{T_{2u}} + \frac{1}{T_{2x}} + (D_v+D_y)\frac{(\gamma G^{(p)}TE^{(p)})^2}{12}}$$

and $\beta_{kn}^{(p)} = \frac{1}{T_{2u}} + \frac{1}{T_{2x}} + (D_v+D_y)\frac{(\gamma G^{(p)}TE^{(p)})^2}{12}$, $$b_k^{(p)} = \int_{T_{start}^{(p)}}^{T_{end}^{(p)}} g(t) e^{-\frac{t}{T_{2x}}} e^{-\left[D_y\frac{(\gamma G^{(p)}TE^{(p)})^2}{12}\right]t} dt \quad (9\text{-}2)$$

where
$C_{kn}^{(p)}$ denotes the element at the $k^{th}$ row and $n^{th}$ column of matrix $C^{(p)}$ in Equation (8);
$b_k^{(p)}$ is the $k^{th}$ element of the vector $B^{(p)}$ in Equation (8);
k=1, 2, . . . , I·J;
n=1, 2, . . . , I·J;
I and J are the number of bins of $T_2$ and D, respectively;
$T_{2u}$ stands for the $u^{th}$ bin of $T_2$ and $T_{2x}$ for the $x^{th}$ bin of $T_2$;
$D_v$ stands for the $v^{th}$ bin of D and $D_y$ for the $y^{th}$ bin of D;
The subscripts u, v, x, and y are defined by $$u = n - \text{int}\left(\frac{n-1}{J}\right)\cdot J; \, v = \text{int}\left(\frac{n-1}{I}\right) + 1;$$

$$x = k - \text{int}\left(\frac{k-1}{I}\right)\cdot I; \, y = \text{int}\left(\frac{k-1}{I}\right) + 1;$$

here the function int(Z) takes the integer part of Z.

The integration limits $T_{start}^{(p)}$ and $T_{end}^{(p)}$ are the start and end time of the $p^{th}$ echo train with wait time $T_w^{(p)}$. For $b_k^{(p)}$ calculations, as long as g(t) can be approximated by integrable functions, the integration can be conducted analytically. Such integrable functions can include, but are not limited to, linear interpolation functions, S-Spline interpolation functions, or exponential interpolation functions. In this way, the elements calculation for each matrix $C^{(p)}$ and each vector $B^{(p)}$ can not only be much faster, saving thousands of multiplication operations for each of the thousands of elements in each echo train processing, but also avoid accumulated quantitative errors.

Figure 6:
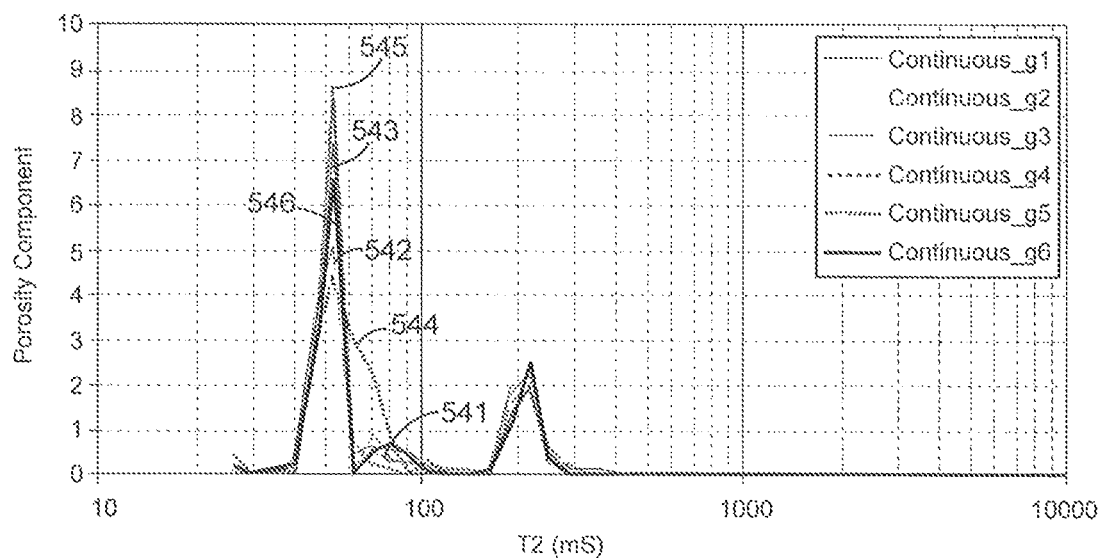
FIG. 6 illustrates an inverted transversal relaxation time distribution by application of an example continuous function method for an echo train, in accordance with various embodiments.
Figure 7:
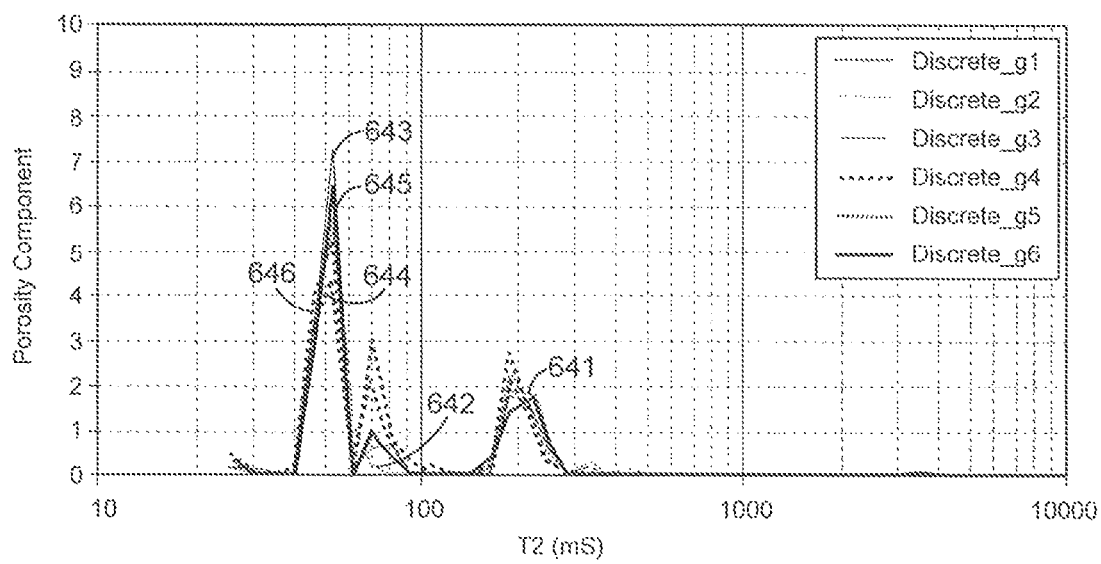
FIG. 7 illustrates an inverted transversal relaxation time distribution provided by application of the discrete space method for the same echo train of FIG. 6.

FIG. 6 illustrates example application of an embodiment of a continuous function method in the NMR inversion for a simulated echo train. Curves 541, 542, 543, 544, 545, and 546 show porosity components for six different continuous functions $g_1(t)$, $g_2(t)$, $g_3(t)$, $g_4(t)$, $g_5(t)$, and $g_6(t)$. FIG. 7 illustrates an application of the discrete space method in the NMR inversion for the same simulated echo train. Curves 641, 642, 643, 644, 645, and 646 show porosity components for sets of discrete points $g_1$, $g_2$, $g_3$, $g_4$, $g_5$, and $g_6$ from which the different continuous functions $g_1(t)$, $g_2(t)$, $g_3(t)$, $g_4(t)$, $g_5(t)$, and $g_6(t)$ are respectively generated. FIGS. 6 and 7 are shown to demonstrate the appropriateness of the new continuous function method relate to the discrete space method by employing both methods to solve a T2 inversion problem. In this comparison, the artificial echo train was generated with added white noise, without taking actual measurements, in which two modes at T2=50 ms and T2=200 ms are pre-set. The inverted T2 distributions provided by both methods obtain reasonable results, correctly finding these two pre-set modes. Comparison of the results from FIGS. 6 and 7 provides a verification of the applicability of the continuous function method.

Figure 8:
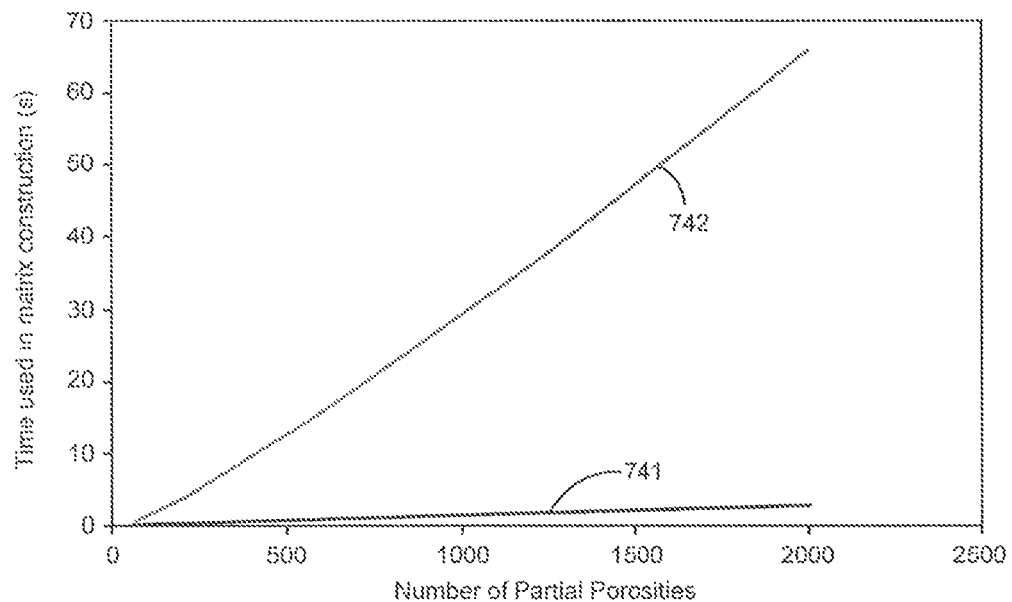
FIG. 8 shows comparisons of matrix construction time for an example continuous function method and a discrete space method, in accordance with various embodiments.

FIG. 8 shows comparisons of matrix construction time for an example embodiment of a continuous function method (curve 741) and a discrete space method (curve 742) in each measurement sequences. These comparisons provide speed comparisons that show enhancements provided by the continuous function method. For an example, suppose five echo trains are measured in each sequence and 1000 echoes are recorded in each train. FIG. 8, along with Table 1, shows recorded time used in matrix construction in the discrete space method and in the continuous function space method, where the unknown partial porosities increase from 54 to 2000. It can be seen that the new continuous function space approach can be 25 times faster than the discrete space method for 2000 unknowns, which is similar to a two-dimensional (2D) inversion case. The continuous function space approach may also be faster for 2.5 or 3 dimensional inversion.

TABLE 1

Processing time comparison in each measurement sequence

| Number of Echo Trains | Number of Echoes in each echo train | Number of unknown partial porosities | Time used in matrix construction (S) in Discrete Space | Time used in matrix construction (S) in Continuous Space |
|---|---|---|---|---|
| 5 | 1000 | 54 | 0.315 | 0.155 |
| 5 | 1000 | 200 | 3.35 | 0.31 |
| 5 | 1000 | 500 | 12.4 | 0.625 |
| 5 | 1000 | 1000 | 28.55 | 1.17 |
| 5 | 1000 | 2000 | 65.39 | 2.65 |

It is noticed that the intercho spacing, TE, in equation (2) is a constant in an echo train. Thus, the sample times $t_1$=TE, $t_2$=2TE, ..., $t_L$=L·TE, the integration operation in equation (8) and equations (9-1) and (9-2) can be solved equivalently by series summation, and the derived formulas are shown in equations (10-1), (10-2), and (10-3), $$c_{kn}^{(p)} = \left(1 - e^{-\frac{T_w^{(p)}}{RT_{2u}}}\right) \cdot TE^{(p)} \cdot \quad (10\text{-}1)$$

$$\left[e^{-\beta_{kn}^{(p)} \cdot TE^{(p)}} + \left(e^{-\beta_{kn}^{(p)} \cdot TE^{(p)}}\right)^2 + \ldots + \left(e^{-\beta_{kn}^{(p)} \cdot TE^{(p)}}\right)^{L^{(p)}}\right]$$

$$= \left(1 - e^{-\frac{T_w^{(p)}}{RT_{2u}}}\right) \cdot TE^{(p)} \cdot \frac{e^{-\beta_{kn}^{(p)} \cdot TE^{(p)}} \cdot \left(1 - e^{-\beta_{kn}^{(p)} \cdot L^{(p)} \cdot TE^{(p)}}\right)}{1 - e^{-\beta_{kn}^{(p)} \cdot TE^{(p)}}}$$

$$b_k^{(p)} = \sum_{l=1}^{L^{(p)}} g_l \cdot TE^{(p)} \cdot e^{-l \cdot TE^{(p)} \cdot \alpha_k^{(p)}} \quad (10\text{-}2)$$

where $$\beta_{kn}^{(p)} = \frac{1}{T_{2u}} + \frac{1}{T_{2x}} + (D_v + D_y)\frac{(\gamma G^{(p)} TE^{(p)})^2}{12}, \text{ and} \quad (10\text{-}3)$$

$$\alpha_k^{(p)} = \frac{1}{T_{2x}} + D_y \frac{(\gamma G^{(p)} TE^{(p)})^2}{12}$$

The subscripts u, v, x, and y are the same as in equations (9-1) and (9-2). The matrix elements in Equation (8) can still be calculated analytically, obtaining the same features of the integration method described by equations (9-1) and (9-2). Since the typical NMR logging data are obtained using the Carr-Purcell-Meiboom-Gill (CPMG) sequence, where the interecho spacing is a constant for the entire echo train, the series summation method provides a straight forward useful tool and requires no interpolation of data.

In various embodiments, processing can be performed to provide a fast method for the determination of a regularization factor. This processing method provides an estimation of the optimal α. In the discussions to follow, the parabolic shaped curve method is used as an example to illustrate how an example embodiment of a method to estimate the regularization factor works quickly in determining the correlation of $\|Ax(\alpha)-B\|\sim\alpha$ and the correlation of $\|x(\alpha)\|\sim\alpha$. As previously noted, the entries of the regularization matrix W in equations (3) through (8) can be functions of the regularization factor α, where α can be solved by minimizing the function d(α), defined in equation (6), with respect to α. However, such an embodiment to estimate the regularization factor also works quickly for L-Curve method.

Figure 9:
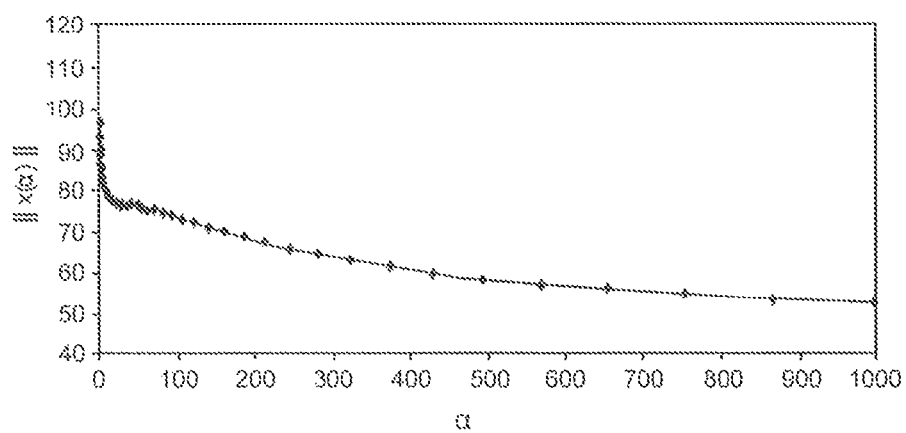
FIG. 9 shows a norm of a solution vector as a function of a regularization factor, in accordance with various embodiments.
Figure 10:
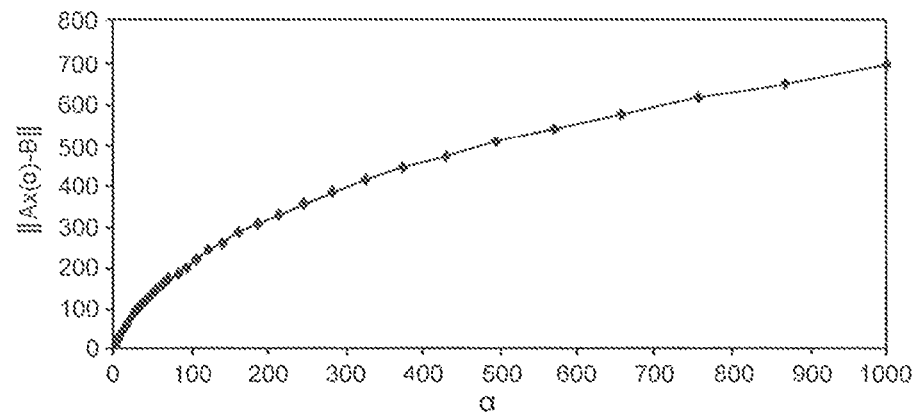
FIG. 10 shows a norm of an error vector as a function of a regularization factor, in accordance with various embodiments.

Mathematically, the norm of the solution vector $\|x(\alpha)\|$ is a monotonically decreasing function of α, shown in FIG. 9. The norm of the error vector $\|Ax(\alpha)-B\|$ is a monotonically increasing function of α, as shown in FIG. 10. Multiple points are needed to determine each of the two curves. However, modeling the data has revealed that if the correlation $\|x(\alpha)\|\sim\alpha$ and the correlation $\|Ax(\alpha)-B\|\sim\alpha$ are transformed into the double log space, quasi-linear relations are observed, as shown in FIGS. 11 and 12, respectively.

Figure 11:
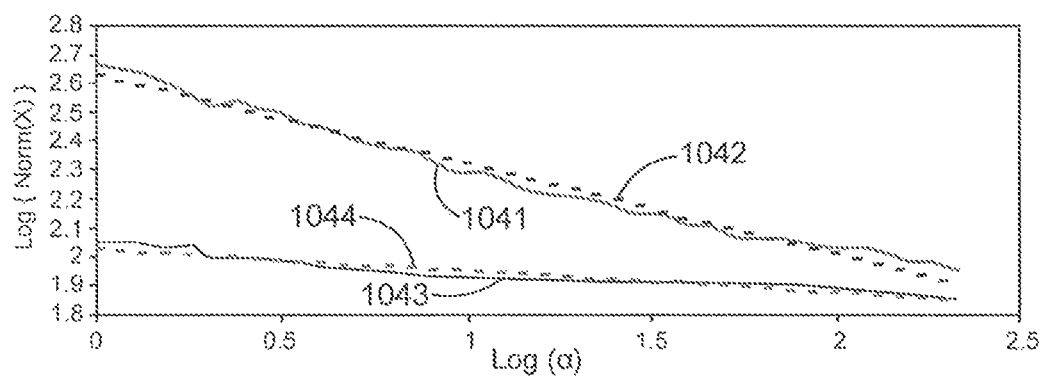
FIG. 11 shows the correlation of the logarithm of the norm of a solution vector with respect to the logarithm of the regularization factor, in accordance with various embodiments.

FIG. 11 shows the correlation of $\text{Log}(\|x(\alpha)\|)$ with respect to $\text{Log}(\alpha)$ for the regularization factor. These curves show the effect of different noise levels. Solid curve 1041 is for a signal-to-noise ratio (SNR) of 7.5 and the dashed curve 1042 is the linear approximations corresponding to curve 1041 at SNR of 7.5. Solid curve 1043 is for a SNR of 1.5 and the dashed curve 1044 is the linear approximation corresponding to curve 1043 at SNR of 1.5. The modeling results reveal that when the real domain (α, $\|x(\alpha)\|$) is transformed into double logarithmic domain {Log(α), Log($\|x(\alpha)\|$)}, then the Log($\|x(\alpha)\|$) becomes a decreasing quasi-linear function of Log(α), as shown in FIG. 11.

Figure 12:
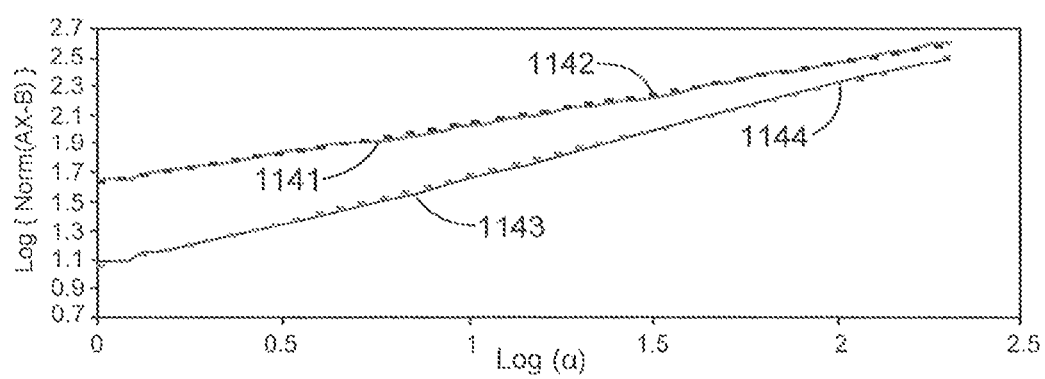
FIG. 12 shows the correlation of the logarithm of the norm of an error vector with respect to the logarithm of the regularization factor, in accordance with various embodiments.

FIG. 12 shows the correlation of $\text{Log}(\|Ax(\alpha)-B\|)$ with respect to Log(α) for the regularization factor. These curves show the effect of different noise levels. Solid curve 1141 is for a signal-to-noise ratio (SNR) of 7.5 and the dashed curve 1142 is the linear approximations corresponding to curve 1141 at SNR of 7.5. Solid curve 1143 is for a SNR of 1.5 and the dashed curve 1144 is the linear approximation corresponding to curve 1143 at SNR of 1.5. Similarly, the modeling results reveal that when the real domain (α, $\|Ax(\alpha)-B\|$) is transformed into double logarithmic domain {Log(α), Log($\|Ax(\alpha)-B\|$)}, the Log($\|Ax(\alpha)-B\|$) also forms an increasing quasi-linear function of Log(α), as shown in FIG. 12.

In various embodiments, a method can predict α, based on the observation of this quasi-linear feature. Such new methods of predicting α can use as few as only two points in the transformed domain instead of a large number of trials currently used. For example, only two α trial values and their corresponding error vectors and solution vector norms can be used to determine the appropriate correlations. The two α points can be enough to construct a linear correlation between Log($\|x(\alpha)\|$) and Log(α) and a linear correlation between Log($\|Ax(\alpha)-B\|$) and Log(α), as follows, $$\text{Log}(\|x(\alpha)\|) = \quad (11)$$
$$\text{Log}(\|x(\alpha_1)\|) + \frac{\text{Log}(\|x(\alpha_2)\|) - \text{Log}(\|x(\alpha_1)\|)}{\text{Log}(\|\alpha_2\|) - \text{Log}(\|\alpha_1\|)}[\text{Log}(\|\alpha\|) - \text{Log}(\|\alpha_1\|)]$$

and, $$\text{Log}(\|Ax(\alpha) - B\|) = \text{Log}(\|Ax(\alpha_1) - B\|) + \quad (12)$$
$$\frac{\text{Log}(\|Ax(\alpha_2) - B\|) - \text{Log}(\|Ax(\alpha_1) - B\|)}{\text{Log}(\|\alpha_2\|) - \text{Log}(\|\alpha_1\|)}[\text{Log}(\|\alpha\|) - \text{Log}(\|\alpha_1\|)]$$

where $\alpha_1$ and $\alpha_2$ can be any two different values in the right range for the problem. Once the values of Log($\|x(\alpha_1)\|$), Log($\|x(\alpha_2)\|$), Log($\|Ax(\alpha_1)-B\|$), and Log($\|Ax(\alpha_2)-B\|$) are calculated, the optimal α can be uniquely determined. By inversely transforming the Log($\|x(\alpha)\|$) and Log($\|Ax(\alpha)-B\|$) from equations (11) and (12), back into the real domain ($\|Ax(\alpha)-B\|$, $\|x(\alpha)\|$), the following are obtained:

$$\|x(\alpha)\| = \exp\left\{\text{Log}(\|x(\alpha_1)\|) + \right. \quad (13)$$
$$\left. \frac{\text{Log}(\|x(\alpha_2)\|) - \text{Log}(\|x(\alpha_1)\|)}{\text{Log}(\|\alpha_2\|) - \text{Log}(\|\alpha_1\|)}[\text{Log}(\|\alpha\|) - \text{Log}(\|\alpha_1\|)]\right\}$$

and $$\|Ax(\alpha) - B\| = \quad (14)$$
$$\exp\left\{\text{Log}(\|Ax(\alpha_1) - B\|) + \frac{\text{Log}(\|Ax(\alpha_2) - B\|) - \text{Log}(\|Ax(\alpha_1) - B\|)}{\text{Log}(\|\alpha_2\|) - \text{Log}(\|\alpha_1\|)}\right.$$
$$\left. [\text{Log}(\|\alpha\|) - \text{Log}(\|\alpha_1\|)]\right\}$$

Substituting equations (13) and (14) into equation (6), the d(α)~α relation can be obtained by only two calculated α points. However, in the presence of heavy noise, more alpha points may be needed to derive reliable results through the linear precession algorithm.

As an example based on the observation of this quasi-linear feature using two points, two points can be arbitrarily picked to start, for example α=1 and α=210. Next, the linear correlation between Log(‖Ax(α)−B‖) and Log(α) and between Log(‖x(α)‖) and Log(α), according to equations (11) and (12), can be derived with these two points. By inversely transforming the Log(‖x(α)‖) and Log(‖Ax(α)−B‖) back into the real domain (‖Ax(α)−B‖, ‖x(α)‖), the optimal α value can be found by minimizing, $$d(\alpha)=\sqrt{\|Ax(\alpha)-B\|^2+\|x(\alpha)\|^2}.$$

Figure 13:
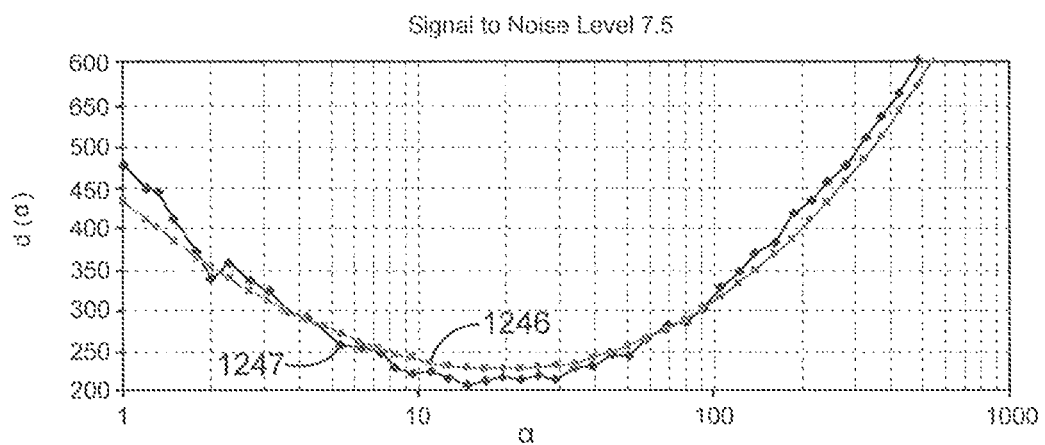
FIG. 13 shows a comparison using an example linear approximation in a double log space with respect to using a multipoint approach in a parabolic curve method, in accordance with various embodiments.

FIG. 13 shows a comparison using an example embodiment of a linear approximation in a double log space with respect to using a multipoint approach in a parabolic curve method. This comparison uses simulated data for the two procedures. The smooth d(α) curve 1246 in FIG. 13 is derived from an example embodiment of a linear approximation in a double log space described above. Curve 1247 in FIG. 13 is derived from the multipoint approach. The results derived from the linear approximation in the double log space in curve 1246 compares very well with the approach of a multiple-alpha point calculation in curve 1247. The value corresponding to the minimal d(α) provides the predicted alpha value. In FIG. 13, the optimal alpha is located at the bottom of the curves.

Figure 14:
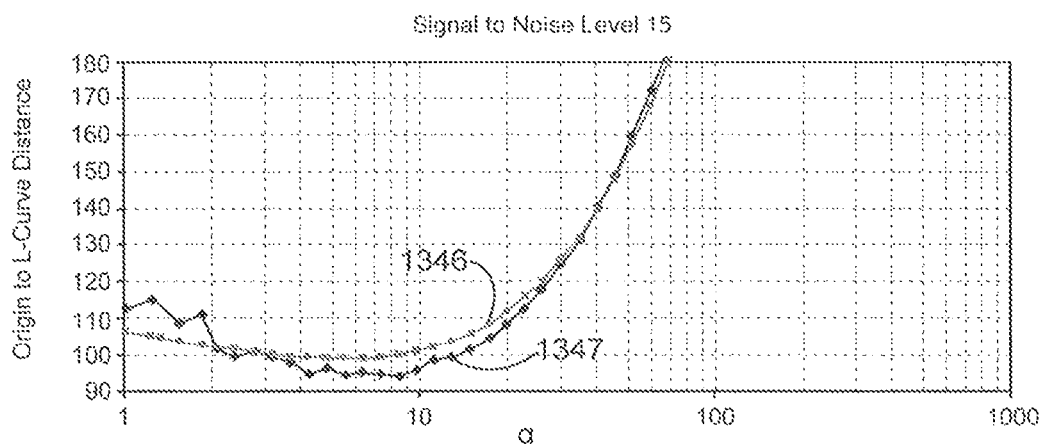
FIG. 14 shows a comparison using an example linear approximation in a double log space with respect to using a multipoint approach in an L-curve method, in accordance with various embodiments.

FIG. 14 shows a comparison using an example linear approximation in a double log space with respect to using a multipoint approach in an L-curve method. This comparison uses simulated data for the two procedures. The smooth d(α) curve 1346 in FIG. 14 is derived from an example embodiment of a linear approximation in a double log space described above. Curve 1347 in FIG. 14 is derived from the multipoint approach. The results derived from the linear approximation in the double log space in curve 1346 compares very well with the approach of a multiple-alpha point calculation in curve 1347. The plot of the distance from the origin to the L-curve as a function of alpha is used to obtain the predicted alpha value.

Figure 15:
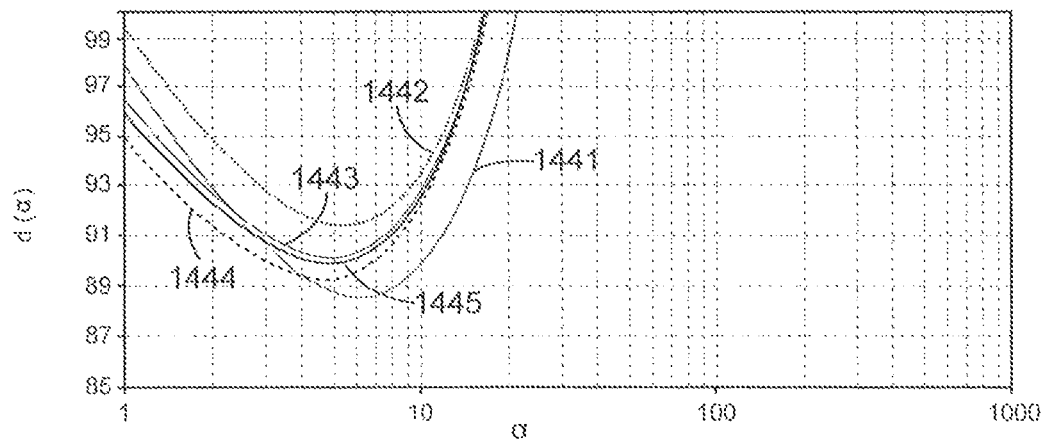
FIG. 15 shows the effects of using a different number of alpha points in a linear approximation in double log space to determine an optimal alpha value in a parabolic curve method, in accordance with various embodiments.

FIG. 15 shows the effects of using a different number of α points in a linear approximation in double log space to determine an optimal α value in a parabolic curve method. This comparison with respect to using different numbers of α points employs simulated data for the procedures. Curve 1441 uses two α points in the linear approximation in double log space. Curve 1442 uses five α points in the linear approximation in double log space. Curve 1443 uses 20α points in the linear approximation in double log space. Curve 1444 uses thirty-five α points in the linear approximation in double log space. Curve 1445 uses fifty α points in the linear approximation in double log space. The simulated data shows that with the increase of alpha points used, the optimal α converges to a fixed value.

Figure 16:
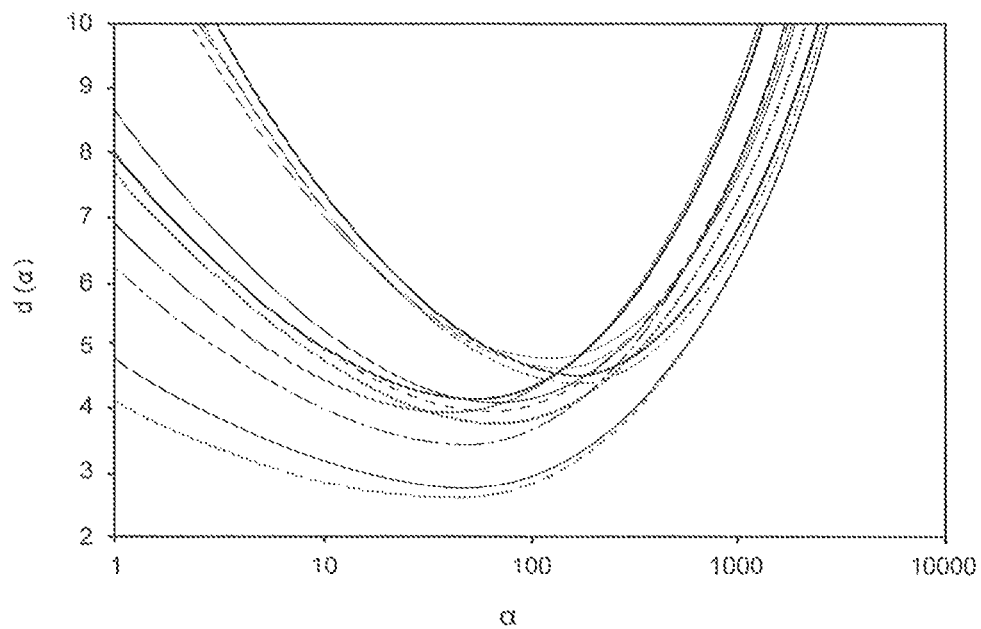
FIG. 16 shows a number of curves simulated for different noise characteristics, in accordance with various embodiments.

FIG. 16 shows a number of curves simulated for different noise characteristics. These curves of d(α) as a function of α indicate that the optimal α is sensitive to noise.

In various embodiments, a processing unit can be configured to perform a number of tasks relative to NMR measurements. These tasks can include conducting an optimization method in the continuous function space to perform NMR inversion instead of discrete space optimization that does not use analytical functions. The completion of these tasks can consequentially derive analytical solutions to the optimization matrix elements, which can greatly reduce the processing time. This process can be especially significant for 2D and 3D NMR inversions. In addition, the tasks can include performing procedures to predict the regularization factor α of a regularization matrix that uses much fewer α points for α optimization than multipoint methods, which can significantly speed up the NMR data inversion.

In various embodiments, components of a system operable to conduct an inversion process on discrete data from measurements, where the system uses an optimization procedure conducted in a continuous function space as described herein or in a similar manner, can be realized in combinations of hardware and software based implementations. These implementations can include a machine-readable storage device having machine-executable instructions, such as a computer-readable storage device having computer-executable instructions, to collect data from one or more measurements of a structure; apply a processing unit to the data forming an optimization relationship such that elements of the optimization relationship are analytically calculable based on the use of an integrable function in the optimization relationship; and apply the processing unit to extract properties of the structure corresponding to the collected data. The data may exhibit multi-exponential decay. The decay curves may be equally spaced decay curves. The integrable function can be derived from the collected data. Deriving the integrable function can be conducted by generating an integrable interpolation function from the data. Generating the integrable interpolation function can include generating one or more of a linear interpolation function, an S-Spline interpolation function, or exponential interpolation function.

In various embodiments, components of a system operable to conduct an inversion process on nuclear magnetic resonance measurements, where the system uses an optimization procedure conducted in a continuous function space as described herein or in a similar manner, can be realized in combinations of hardware and software based implementations. These implementations can include a machine-readable storage device having machine-executable instructions, such as a computer-readable storage device having computer-executable instructions, to collect data from measured echo trains in a nuclear magnetic resonance measurement procedure conducted on a region of a borehole; apply a processing unit to the data forming an optimization relationship including unknown partial porosities of the region such that elements of the optimization relationship are analytically calculable based on the use of an integrable function in the optimization relationship; and apply the processing unit to extract properties of the region corresponding to the collected data. The integrable function can be derived from the collected data.

Implementations can include a machine-readable storage device having machine-executable instructions, such as a computer-readable storage device having computer-executable instructions, to collect data from measured echo trains in a nuclear magnetic resonance measurement procedure conducted on a region of a borehole; and to operate a processing unit such that the processing unit conducts operations to process the nuclear magnetic resonance data. These operations can include: operating on the data forming an optimization relationship including unknown partial porosities of the region and a regularization matrix such that a vector of the unknown partial porosities and an error vector are based on a regularization factor, the error vector generated from the optimization relationship; generating a first linear correlation between the logarithm corresponding to the vector of the unknown partial porosities and a logarithm corresponding to the regularization factor using a number of initially selected values of the regularization factor, generating a second linear correlation between a logarithm corresponding to the error vector and the logarithm corresponding to the regularization factor using the number of initially selected values of the regularization factor; generating a first vector of the unknown partial porosities based on the first linear correlation and generating a second error vector based on the second linear correlation; generating points of a curve using the first vector and the second error vector and determining an approximately optimal value of the regularization factor using the points of the curve, the approximately optimal value applied to the optimization relationship to conduct an inversion of the data; and extracting properties of the region corresponding to the collected data from the inversion.

Executed instructions can also include instructions to operate a tool having one or more transmitters and one or more receivers of a nuclear magnetic resonance tool to provide data to a processing unit such that the processing unit conducts one or more processes in accordance with the teachings herein. Further, a machine-readable storage device, herein, is a physical device that stores data represented by physical structure within the device. Examples of machine-readable storage devices include, but are not limited to, read only memory (ROM), random access memory (RAM), a magnetic disk storage device, an optical storage device, a flash memory, and other electronic, magnetic, and/or optical memory devices.

Figure 17:
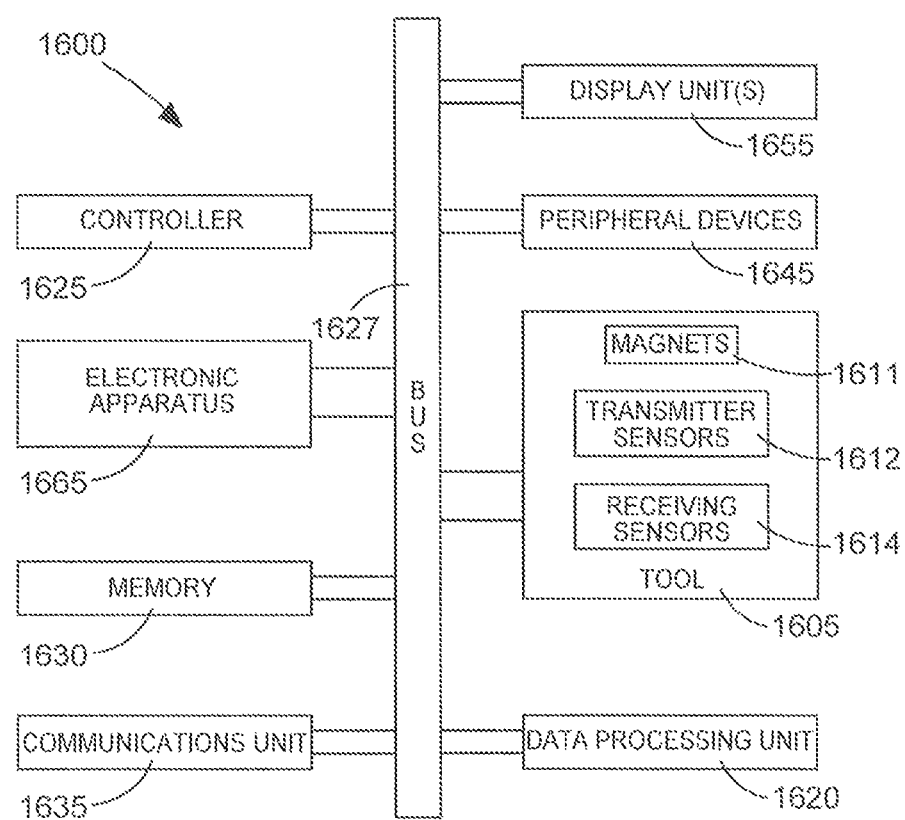
FIG. 17 depicts a block diagram of features of an example system having a processing unit operable to provide nuclear magnetic resonance inversion by optimization in continuous function space, in accordance with various embodiments.

FIG. 17 depicts a block diagram of features of an example embodiment of a system 1600 operable to provide nuclear magnetic resonance inversion by optimization in continuous function space, as described herein or in a similar manner. The system 1600 can include a tool 1605 having an arrangement of magnets 1611, transmitter sensors 1612, and receiver sensors 1614 that can be realized in a similar or identical manner to arrangements of sensors discussed herein. The system 1600 can be configured to operate in accordance with the teachings herein.

The system 1600 can include a controller 1625, a memory 1630, an electronic apparatus 1665, and a communications unit 1635. The memory 1630 can be structured to include a database. The controller 1625, the memory 1630, and the communications unit 1635 can be arranged to operate as a processing unit to control operation of the transmitters 1612 and the receivers 1614 and to perform operations on the signals collected by the receivers 1614 to conduct nuclear magnetic resonance inversion by optimization in continuous function space, in a manner similar or identical to the procedures discussed herein. A processing unit 1620, structured to conduct nuclear magnetic resonance inversion by optimization in continuous function space, can be implemented as a single unit or distributed among the components of the system 1600 including electronic apparatus 1665. The controller 1625 and the memory 1630 can operate to control activation of the transmitters 1612 and selection of the receiver sensors in the tool 1605 and to manage processing schemes in accordance with measurement procedures and signal processing as described herein. The processing unit 1620 and other components of the system 1600 can be configured, for example, to operate similar to or identical to the components discussed herein or similar to or identical to any of methods discussed herein.

The communications unit 1635 can include downhole communications for appropriately located sensors in a drilling operation. Such downhole communications can include a telemetry system. The communications unit 1635 may use combinations of wired communication technologies and wireless technologies at frequencies that do not interfere with on-going measurements.

The system 1600 can also include a bus 1627, where the bus 1627 provides electrical conductivity among the components of the system 1600. The bus 1627 can include an address bus, a data bus, and a control bus, each independently configured or in an integrated format. The bus 1627 can be realized using a number of different communication mediums that allows for the distribution of components of the system 1600. Use of the bus 1627 can be regulated by the controller 1625.

In various embodiments, the peripheral devices 1645 can include additional storage memory and other control devices that may operate in conjunction with the controller 1625 and the memory 1630. In an embodiment, the controller 1625 can be realized as a processor or a group of processors that may operate independently depending on an assigned function.

The system 1600 can include display unit(s) 1655 as a distributed component on the surface at a drilling operation, which can be used with instructions stored in the memory 1630 to implement a user interface to monitor the operation of the tool 1605 or components distributed within the system 1600. The user interface may be used to input parameter values for thresholds such that the system 1600 can operate autonomously substantially without user intervention. The user interface can also provide for manual override and change of control of the system 1600 to a user. Such a user interface can be operated in conjunction with the communications unit 1635 and the bus 1627.

Figure 18:
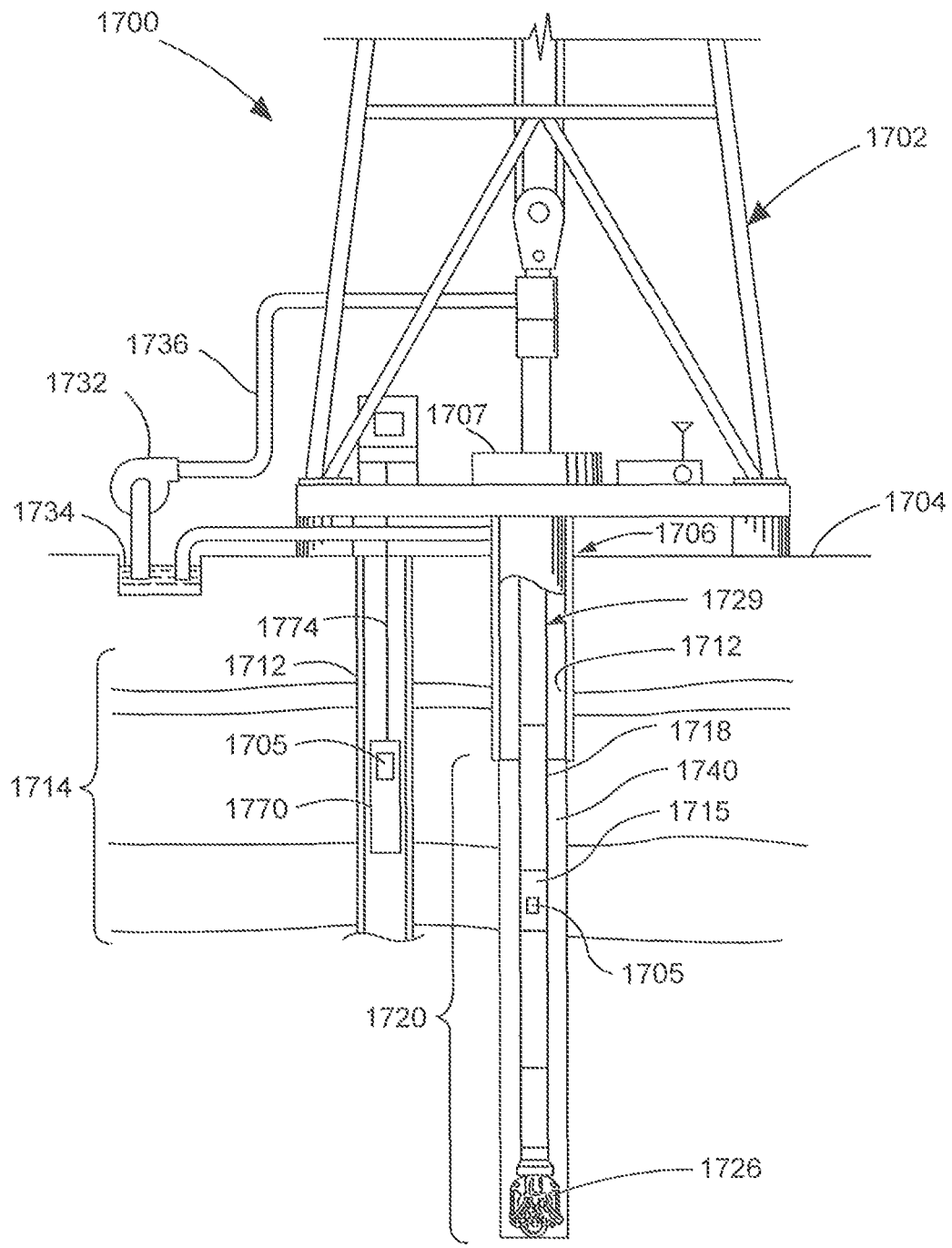
FIG. 18 depicts an example system at a drilling site, where the system includes a tool configured with a processing unit operable to provide nuclear magnetic resonance inversion by optimization in continuous function space, in accordance with various embodiments.

FIG. 18 depicts an embodiment of a system 1700 at a drilling site, where the system 1700 includes a tool 1705 having a processing unit operable to provide nuclear magnetic resonance inversion by optimization in continuous function space. The tool 1705 can be distributed among the components of system 1700. The tool 1705 can be realized in a similar or identical manner to arrangements of control units, transmitters, receivers, and processing units discussed herein. The tool 1705 can be structured and fabricated in accordance with various embodiments as taught herein with respect to transmitters, receivers, control units, and processing units to perform nuclear magnetic resonance inversion by optimization in continuous function space.

The system 1700 can include a drilling rig 1702 located at a surface 1704 of a well 1706 and a string of drill pipes, that is, the drill string 1708, connected together so as to form a drilling string that is lowered through a rotary table 1707 into a wellbore or borehole 1712. The drilling rig 1702 can provide support for the drill string 1708. The drill string 1708 can operate to penetrate the rotary table 1707 for drilling the borehole 1712 through subsurface formations 1714. The drill string 1708 can include drill pipe 1718 and a bottom hole assembly 1720 located at the lower portion of the drill pipe 1718.

The bottom hole assembly 1720 can include a drill collar 1715, the tool 1705 attached to the drill collar 1715, and a drill bit 1726. The drill bit 1726 can operate to create the borehole 1712 by penetrating the surface 1704 and the subsurface formations 1714. The tool 1705 can be structured for an implementation in the borehole 1712 as a MWD system such as a LWD system. The housing containing the tool 1705 can include electronics to activate one or more transmitters of the tool 1705 and collect responses from one or more receivers of the tool 1705. Such electronics can include a processing unit to conduct nuclear magnetic resonance inversion by optimization in continuous function space and provide results to the surface over a standard communication mechanism for operating a well. Alternatively, electronics can include a communications interface to provide signals output by receivers of the tool 1705 to the surface over a standard communication mechanism for operating a well, where these output signals can be analyzed at a processing unit at the surface to conduct nuclear magnetic resonance inversion by optimization in continuous function space in accordance with the teachings herein.

During drilling operations, the drill string 1708 can be rotated by the rotary table 1707. In addition to, or alternatively, the bottom hole assembly 1720 can also be rotated by a motor (e.g., a mud motor) that is located downhole. The drill collars 1715 can be used to add weight to the drill bit 1726. The drill collars 1715 also can stiffen the bottom hole assembly 1720 to allow the bottom hole assembly 1720 to transfer the added weight to the drill bit 1726, and in turn, assist the drill bit 1726 in penetrating the surface 1704 and subsurface formations 1714.

During drilling operations, a mud pump 1732 can pump drilling fluid (sometimes known by those of skill in the art as "drilling mud") from a mud pit 1734 through a hose 1736 into the drill pipe 1718 and down to the drill bit 1726. The drilling fluid can flow out from the drill bit 1726 and be returned to the surface 1704 through an annular area 1740 between the drill pipe 1718 and the sides of the borehole 1712. The drilling fluid may then be returned to the mud pit 1734, where such fluid is filtered. In some embodiments, the drilling fluid can be used to cool the drill bit 1726, as well as to provide lubrication for the drill bit 1726 during drilling operations. Additionally, the drilling fluid may be used to remove subsurface formation 1714 cuttings created by operating the drill bit 1726.

In various embodiments, the tool 1705 may be included in a tool body 1770 coupled to a logging cable 1774 such as, for example, for wireline applications. The tool body 1770 containing the tool 1705 can include electronics to activate one or more transmitters of the tool 1705 and collect responses from one or more receivers of the tool 1705. Such electronics can include a processing unit to conduct nuclear magnetic resonance inversion by optimization in continuous function space and provide results to the surface over a standard communication mechanism for operating a well. Alternatively, electronics can include a communications interface to provide signals output by receivers of the tool 1705 to the surface over a standard communication mechanism for operating a well, where these output signals can be analyzed at a processing unit at the surface to conduct nuclear magnetic resonance inversion by optimization in continuous function space in accordance with the teachings herein. The logging cable 1774 may be realized as a wireline (multiple power and communication lines), a mono-cable (a single conductor), and/or a slick-line (no conductors for power or communications), or other appropriate structure for use in the bore hole 1712.

Although specific embodiments have been illustrated and described herein, it will be appreciated by those of ordinary skill in the art that any arrangement that is calculated to achieve the same purpose may be substituted for the specific embodiments shown. Various embodiments use permutations and/or combinations of embodiments described herein. It is to be understood that the above description is intended to be illustrative, and not restrictive, and that the phraseology or terminology employed herein is for the purpose of description. Combinations of the above embodiments and other embodiments will be apparent to those of skill in the art upon studying the above description.

What is claimed is:

1. A method for using nuclear magnetic resonance to evaluate porosity in a subsurface formation, the method comprising:

placing a nuclear magnetic resonance (NMR) tool having one or more transmitters, receivers and magnets, in a borehole of the subsurface formation;

activating the one or more transmitters of the NMR tool;

utilizing the one or more receivers of the NMR tool, to take one or more measurements of an echo train indicative of exponentially decaying phenomena conducted on a region of the subsurface formation;

generating, by an electronic processing unit, an integrable function wherein the integrable function is based on an interpolation of the measurements of the echo train;

determining, by the electronic processing unit, a first logarithm, wherein the first logarithm is a logarithm of a first partial porosity vector norm, wherein the first partial porosity norm is based on the integrable function at a first regularization factor value;

determining, by the electronic processing unit, a second logarithm, wherein the second logarithm is a logarithm of a second partial porosity vector norm, wherein the second partial porosity norm is based on the integrable function at a second regularization factor value;

determining, by the electronic processing unit, an optimal regularization factor value based on a minimum or maximum of an optimization function, wherein the optimization function comprises a difference between the first logarithm and the second logarithm;

extracting, by the electronic processing unit, properties of the region of the borehole based on the optimal regularization factor value, wherein the one or more properties comprises an optimal partial porosity value.

2. The method of claim 1, wherein the method includes deriving the integrable function by generating an integrable interpolation function from the data.

3. The method of claim 2, wherein generating the integrable interpolation function includes generating one or more of a linear interpolation function, a S-Spline interpolation function, or exponential interpolation function.

4. The method of claim 1, further comprising operating a well to create the borehole based on the extracted properties of the region of the borehole.

5. A method for using nuclear magnetic resonance to evaluate porosity in a subsurface formation, the method comprising:

placing a nuclear magnetic resonance (NMR) tool having one or more transmitters, receivers and magnets, in a borehole of the subsurface formation;

activating the one or more transmitters of the NMR tool;

utilizing the one or more receivers of the NMR tool to take one or more measurements of an echo trains indicative of exponentially decaying phenomena in a nuclear magnetic resonance measurement procedure conducted in the subsurface formation;

generating, by an electronic processing unit, an integrable function, wherein the integrable function is based on an interpolation of the measurements of the echo train;

determining, by an electronic processing unit, a first logarithm, wherein the first logarithm is a logarithm of a first partial porosity vector norm, wherein the first partial porosity vector is based on the integrable function at a first regularization factor value;

determining, by the electronic processing unit, a second logarithm, wherein the second logarithm is a logarithm of a second partial porosity vector norm, wherein the second partial porosity vector is based on the integrable function at a second regularization factor value;

determining, by the electronic processing unit, an optimal regularization factor value based on a minimum or maximum of an optimization function, wherein the optimization function comprises a difference between the first logarithm and the second logarithm; and extracting, by the electronic processing unit, properties of the subsurface formation based on the optimal regularization factor value, wherein the one or more properties comprises an optimal partial porosity value.

6. The method of claim 5, wherein the method includes deriving the integrable function by generating an integrable interpolation function from the data.

7. The method of claim 6, wherein generating the integrable interpolation function includes generating one or more of a linear interpolation function, a S-Spline interpolation function, or exponential interpolation function.

8. The method of claim 5, further comprising forming an optimization matrix relationship in a data storage device.

9. The method of claim 5, wherein the the optimization matrix relationship given by $$\left(\sum_{p=1}^{P} C^{(p)} + W^T W\right) \overline{m} = \sum_{p=1}^{P} B^{(p)}$$

where $C^{(p)}$ is a matrix of a $p^{th}$ echo train, P is a total number of echo trains, $\overline{m}$ is a vector containing the unknown partial porosities, $B^{(p)}$ is a signal vector of the $p^{th}$ echo train having elements $b_k^{(p)}$ based on the integrable function, W is a regularization matrix, $W^T$ is a transpose of the regularization matrix, and each $C^{(p)}$ is a matrix of elements $c_{kn}^{(p)}$ related to parameters of the subsurface formation and the nuclear magnetic resonance measurement procedure.

10. The method of claim 9, wherein $$c_{kn}^{(p)} = \left(1 - e^{-\frac{T_w(p)}{RT_{2u}}}\right) \frac{\left(e^{-\beta_{kn}^{(p)} \cdot T_{start}^{(p)}} - e^{-\beta_{kn}^{(p)} \cdot T_{end}^{(p)}}\right)}{\frac{1}{T_{2u}} + \frac{1}{T_{2x}} + (D_v + D_y)\frac{(\gamma G^{(p)} TE^{(p)})^2}{12}}$$

and $\beta_{kn}^{(p)} = \frac{1}{T_{2u}} + \frac{1}{T_{2x}} + (D_v + D_y)\frac{(\gamma G^{(p)} TE^{(p)})^2}{12}$, $$b_k^{(p)} = \int_{T_{start}^{(p)}}^{T_{end}^{(p)}} g(t) e^{-\frac{t}{T_{2x}}} e^{-\left[D_y \frac{(\gamma G^{(p)} TE^{(p)})^2}{12}\right] t} dt$$

for fluid diffusivities in a number of bins totaling I such that $D_v$ is a fluid diffusivity in a $v^{th}$ bin and D is a fluid diffusivity in a $y^{th}$ bin, for transversal relaxation times in a number of bins totaling J such that $T_{2u}$ is a transversal relaxation time in a $u^{th}$ bin and $T_{2x}$ is a transversal relaxation time in a $x^{th}$ bin, R is a ratio of longitudinal relaxation time and transversal relaxation time, $G^{(p)}$ is a magnetic field gradient of the $p^{th}$ echo train, $\gamma$ is a gyromagnetic ratio, $TE^{(p)}$ is a time spacing between echoes in the $p^{th}$ echo train with wait time $T_w^{(p)}$, $T_{start}^{(p)}$ is a start time of the $p^{th}$ echo train and $T_{end}^{(p)}$ is an end time of the $p^{th}$ echo train, and g(t) is the integrable function derived from the collected data, the subscripts u, v, x, and y are defined by $$u = n - \text{int}\left(\frac{n-1}{J}\right) \cdot J; v = \text{int}\left(\frac{n-1}{I}\right) + 1;$$

$$x = k - \text{int}\left(\frac{k-1}{I}\right) \cdot I; y = \text{int}\left(\frac{k-1}{I}\right) + 1;$$

with function int(Z) takes the integer part of Z.

11. The method of claim 9, wherein spacing between echoes of the echo train are equal with a total of $L^{(p)}$ spacings in the $p^{th}$ echo train such that $$c_{kn}^{(p)} = \left(1 - e^{-\frac{T_w(p)}{RT_{2u}}}\right) \cdot TE^{(p)} \cdot \frac{e^{-\beta_{kn}^{(p)} \cdot TE^{(p)}} \cdot \left(1 - e^{-\beta_{kn}^{(p)} \cdot L^{(p)} \cdot TE^{(p)}}\right)}{1 - e^{-\beta_{kn}^{(p)} \cdot TE^{(p)}}}$$

$$b_k^{(p)} = \sum_{l=1}^{L^{(p)}} g_l \cdot TE^{(p)} \cdot e^{-l \cdot TE^{(p)} \cdot \alpha_k^{(p)}}.$$

where $$\beta_{kn}^{(p)} = \frac{1}{T_{2u}} + \frac{1}{T_{2x}} + (D_v + D_y)\frac{(\gamma G^{(p)} TE^{(p)})^2}{12}, \text{ and}$$

$$\alpha_k^{(p)} = \frac{1}{T_{2x}} + D_y \frac{(\gamma G^{(p)} TE^{(p)})^2}{12}$$

for fluid diffusivities in a number of bins totaling I such that $D_v$ is a fluid diffusivity in a $v^{th}$ bin and $D_y$ is a fluid diffusivity in a $y^{th}$ bin, for transversal relaxation times in a number of bins totaling J such that $T_{2u}$ is a transversal relaxation time in a $u^{th}$ bin and $T_{2x}$ is a transversal relaxation time in a $x^{th}$ bin, R is a ratio of longitudinal relaxation time and transversal relaxation time, $G^{(p)}$ is a magnetic field gradient of the $p^{th}$ echo train, $\gamma$ is a gyromagnetic ratio, $TE^{(p)}$ is a time spacing between echoes in the $p^{th}$ echo train with wait time $T_w^{(p)}$, $T_{start}^{(p)}$ is a start time of the $p^{th}$ echo train and $T_{end}^{(p)}$ is an end time of the $p^{th}$ echo train, and $g_l$ is an $l^{th}$ value derived from the collected data, the subscripts u, v, x, and y are defined by $$u = n - \text{int}\left(\frac{n-1}{J}\right) \cdot J; v = \text{int}\left(\frac{n-1}{I}\right) + 1;$$

$$x = k - \text{int}\left(\frac{k-1}{I}\right) \cdot I; y = \text{int}\left(\frac{k-1}{I}\right) + 1;$$

with function int(Z) takes the integer part of Z.

12. A method for using nuclear magnetic resonance to evaluate porosity in a geological formation, the method comprising:

placing, by a nuclear magnetic resonance tool (NMR) having one or more transmitters, receivers and magnets, in a borehole of the geological formation;

activating the one or more transmitters of the NMR tool;

utilizing the one or more receivers of the NMR tool to take one or more measurements of an echo train indicative of an exponentially decaying phenomena in a nuclear magnetic resonance measurement procedure conducted on a region of the borehole;

forming, by an electronic processing unit, an integrable function wherein the integrable function is based on an interpolation of measurements of the echo train and wherein the integrable function comprises a regularization factor;

generating, by the electronic processing unit, a first logarithm associated with a first vector of partial porosities which is based on the integrable function at a first regularization factor value;

generating, by the electronic processing unit, a second logarithm associated with a second vector of partial porosities which is based on the integrable function at a second regularization factor value;

generating, by the electronic processing unit, a third logarithm associated with a first error vector which is based on the first regulation factor;

generating, by the electronic processing unit, a fourth logarithm associated with a second error vector which is based on the second regulation factor;

determining, by the electronic processing unit, an optimal value of the regularization factor using an optimal regularization factor value based on a minimum or maximum of an optimization function, wherein the optimization function comprises a difference between the first logarithm and the second logarithm and a difference between the third logarithm and the fourth logarithm; and extracting, by the electronic processing unit, properties of the region based on the optimal regularization factor value, wherein the one or more properties comprises an optimal partial porosity value.

13. The method of claim 12, wherein the first logarithm corresponding to the first vector of partial porosities is a logarithm of a norm of the first vector of the partial porosities and the third logarithm corresponding to the first error vector is a logarithm of a norm of the first error vector.

14. The method of claim 12, wherein a first correlation is given by $$\text{Log}(\|x(\alpha)\|) = \text{Log}(\|x(\alpha_1)\|) + \frac{\text{Log}(\|x(\alpha_2)\|) - \text{Log}(\|x(\alpha_1)\|)}{\text{Log}(\|\alpha_2\|) - \text{Log}(\|\alpha_1\|)}[\text{Log}(\|\alpha\|) - \text{Log}(\|\alpha_1\|)]$$

and a second correlation is given by $$\text{Log}(\|Ax(\alpha) - B\|) = \text{Log}(\|Ax(\alpha_1) - B\|) + \frac{\text{Log}(\|Ax(\alpha_2) - B\|) - \text{Log}(\|Ax(\alpha_1) - B\|)}{\text{Log}(\|\alpha_2\|) - \text{Log}(\|\alpha_1\|)}[\text{Log}(\|\alpha\|) - \text{Log}(\|\alpha_1\|)]$$

where $\alpha_1$ and $\alpha_2$ correspond to the first regulation factor and the second regulation factor, $x(\alpha)$ is a given vector of the partial porosities and $Ax(\alpha) - B$ is a given error vector.

15. The method of claim 12, wherein the optimization function is based on using the first logarithm and the third logarithm to generate an L-curve to determine the optimal regularization factor value or using the first logarithm and the third logarithm to generate a parabolic curve to determine the optimal regularization factor value.

16. The method of claim 15, wherein using the first logarithm and the second logarithm to generate the parabolic curve includes forming the relationship $$d(\alpha) = \sqrt{\|Ax(\alpha) - B\|^2 + \|x(\alpha)\|^2},$$

where $x(\alpha)$ is a given vector of the unknown partial porosities and $Ax(\alpha) - B$ is a given error vector.

17. A non-transitory machine-readable storage device for using nuclear magnetic resonance to evaluate porosity in a subsurface formation, the device having instructions stored thereon, which, when performed by a machine, cause the machine to perform operations, the operations comprising:

collecting, by a nuclear magnetic resonance tool having one or more transmitters, receivers and magnets, data from one or more measurements of an echo train indicative of exponentially decaying phenomena in the subsurface formation;

generating an integrable function wherein the integrable function is based on an interpolation of the one or more measurements of the echo train, and wherein the integrable function comprises a regularization factor;

determining a first logarithm, wherein the first logarithm is a logarithm of a first partial porosity vector norm, wherein the first partial porosity vector norm is based on the integrable function at a first regularization factor value;

determining a second logarithm, wherein the second logarithm is a logarithm of a second partial porosity vector norm, wherein the second partial porosity vector norm is based on the integrable function at a second regularization factor value;

determining an optimal regularization factor value based on a minimum or maximum of an optimization function, wherein the optimization function comprises a difference between the first logarithm and the second logarithm;

based on the optimization relationship, extracting properties of the subsurface formation based on the optimal regularization factor value, wherein the one or more properties comprises an optimal partial porosity value.

18. A system for using nuclear magnetic resonance to evaluate porosity in a subsurface formation, the system comprising:

a nuclear magnetic resonance (NMR) tool having one or more transmitters, receivers and magnets;

an electronic processing unit structured to collect, using the NMR tool, data from the one or more measurements of an echo train indicative of exponentially decaying phenomena in the subsurface formation;

generate an integrable function wherein the integrable function is based on an interpolation of the one or more measurements of the echo train derived from the collected data;

determine a first logarithm, wherein the first logarithm is a logarithm of a first partial porosity vector norm, wherein the first partial porosity vector norm is based on the integrable function at a first regularization factor value;

determine a second logarithm, wherein the second logarithm is a logarithm of a second partial porosity vector norm, wherein the second partial porosity vector norm is based on the integrable function at a second regularization factor value;

determine an optimal regularization factor value based on a minimum or maximum of an optimization function, wherein the optimization function comprises a difference between the first logarithm and the second logarithm; and atoll extract properties of the subsurface formation based on the optimal regularization factor value, wherein the one or more properties comprises an optimal partial porosity value.

19. The system of claim 18, the collected data is data collected from the measured echo trains in a nuclear magnetic resonance measurement procedure conducted on the subsurface formation around a borehole.

20. The system of claim 18, wherein the electronic processing unit is structured to derive the integrable function by generation of an integrable interpolation function from the collected data.

21. The system of claim 20, wherein generation of the integrable interpolation function includes generation one or more of a linear interpolation function, a S-Spline interpolation function, or exponential interpolation function.

22. The system of claim 19, wherein the electronic processing unit is structured to use an optimization matrix relationship given by $$\left(\sum_{p=1}^{P} C^{(p)} + W^T W\right) \overline{m} = \sum_{p=1}^{P} B^{(p)}$$

where $C^{(p)}$ is a matrix of a $p^{th}$ echo train, P is a total number of echo trains, $\overline{m}$ is a vector containing the unknown partial porosities, $B^{(p)}$ is a signal vector of the $p^{th}$ echo train having elements $b_k^{(p)}$ based on the integrable function, W is a regularization matrix, $W^T$ is a transpose of the regularization matrix, and each $C^{(p)}$ is a matrix of elements $c_{kn}^{(p)}$ related to parameters of the region and a nuclear magnetic resonance measurement procedure.

23. The system of claim 18, wherein a first correlation is given by $$\text{Log}(\|x(\alpha)\|) = \text{Log}(\|x(\alpha_1)\|) + \frac{\text{Log}(\|x(\alpha_2)\|) - \text{Log}(\|x(\alpha_1)\|)}{\text{Log}(\|\alpha_2\|) - \text{Log}(\|\alpha_1\|)} [\text{Log}(\|\alpha\|) - \text{Log}(\|\alpha_1\|)]$$

and a second correlation is given by $$\text{Log}(\|Ax(\alpha) - B\|) = \text{Log}(\|Ax(\alpha_1) - B\|) + \frac{\text{Log}(\|Ax(\alpha_2) - B\|) - \text{Log}(\|Ax(\alpha_1) - B\|)}{\text{Log}(\|\alpha_2\|) - \text{Log}(\|\alpha_1\|)} [\text{Log}(\|\alpha\|) - \text{Log}(\|\alpha_1\|)]$$

where $\alpha_1$ and $\alpha_2$ are the first and second regularization factor respectively, $x(\alpha)$ is a given vector of the unknown partial porosities and $Ax(\alpha)-B$ is a given error vector.

24. The system of claim 18, wherein the optimization function is based on using the first logarithm and the second logarithm to generate an L-curve to determine the optimal regularization factor value or using the first logarithm and the second logarithm to generate a parabolic curve to determine the optimal regularization factor value.

25. The system of claim 24, wherein use of the first logarithm and the second logarithm to generate the parabolic curve includes formation of the relationship $$d(\alpha) = \sqrt{\|Ax(\alpha) - B\|^2 + \|x(\alpha)\|^2},$$

where $x(\alpha)$ is a given vector of the unknown partial porosities and $Ax(\alpha)-B$ is a given error vector.

\* \* \* \* \*

UNITED STATES PATENT AND TRADEMARK OFFICE
CERTIFICATE OF CORRECTION

PATENT NO. : 10,042,026 B2
APPLICATION NO. : 14/414031
DATED : August 7, 2018
INVENTOR(S) : Jing Li et al.

Page 1 of 1

It is certified that error appears in the above-identified patent and that said Letters Patent is hereby corrected as shown below:

In the Specification

In Column 9, Line 1, please replace "intercho" with "interecho"

Signed and Sealed this
Nineteenth Day of March, 2019

Andrei Iancu
*Director of the United States Patent and Trademark Office*